United States Patent [19]
Kraus et al.

[11] Patent Number: 5,872,278
[45] Date of Patent: Feb. 16, 1999

[54] PREPARATION OF ISOCYANATES HAVING A LIGHT COLOR

[75] Inventors: Rupert Kraus, Waldsee; Martin Reif, Ludwigshafen; Bernd Bruchmann, Freinsheim; Helmut Tesch, Rödersheim-Gronau, all of Germany

[73] Assignee: BASF Aktiengesellschaft, Ludwigshafen, Germany

[21] Appl. No.: 40,673

[22] Filed: Mar. 18, 1998

[30] Foreign Application Priority Data

Mar. 19, 1997 [DE] Germany ............... 197 11 447.4

[51] Int. Cl.$^6$ .................................... C07K 118/02
[52] U.S. Cl. ............................................... 560/347
[58] Field of Search ................................ 560/347

[56] References Cited

U.S. PATENT DOCUMENTS

| | | |
|---|---|---|
| 4,465,639 | 8/1984 | Hatfield, Jr. . |
| 5,364,958 | 11/1994 | Ishida et al. . |

FOREIGN PATENT DOCUMENTS

| | | |
|---|---|---|
| A 0 133 538 A2 | 2/1985 | European Pat. Off. . |
| A 0 445 602 A3 | 9/1991 | European Pat. Off. . |
| A 0 446 781 A3 | 9/1991 | European Pat. Off. . |
| A 0 467 125 A1 | 1/1992 | European Pat. Off. . |
| A 0 546 398 A3 | 11/1992 | European Pat. Off. . |
| A 0 561 225 A3 | 9/1993 | European Pat. Off. . |
| A 0 581 100 A1 | 2/1994 | European Pat. Off. . |
| A 0 538 500 B1 | 2/1995 | European Pat. Off. . |
| A 0 676 391 A1 | 10/1995 | European Pat. Off. . |

*Primary Examiner*—Samuel Barts
*Attorney, Agent, or Firm*—Fernando A. Borrego

[57] ABSTRACT

In a process for preparing isocyanates having a light color by reacting the corresponding amines with phosgene, the amines are treated with solid inorganic substances containing Lewis acid and/or Brönsted acid centers prior to the reaction with the phosgene.

22 Claims, No Drawings

PREPARATION OF ISOCYANATES HAVING A LIGHT COLOR

The present invention relates to a process for preparing isocyanates, in particular polyisocyanates of the diphenylmethane diisocyanate series, which have a light color.

Isocyanates are raw materials for the production of polyurethanes. They are usually prepared by reacting the corresponding amines with phosgene. One of the most widely used isocyanates is diphenylmethane diisocyanate (MDI) and also its higher homologues (usually known as raw MDI).

Owing to the starting amine, which is a mixture of diphenylmethanediamine and polyphenylenepolymethylenepolyamine (MDA), and the MDI production process which comprises reacting the MDA with phosgene and subsequently working up the reaction product after separating off the solvents and distilling off monomeric MDI, the raw MDI obtained has a dark color and leads to polyurethane materials which have a yellowish discoloration. Since these discolorations are regarded as quality defects, there have been many attempts to provide raw MDI having a light color.

Thus, U.S. Pat. No. 5,364,958 describes a process for preparing MDI in which the phosgene is separated off at low temperatures after the phosgenation and the remaining isocyanate is treated with HCl gas to destroy the compounds which cause discoloration, usually known as color precursors.

EP-A-581 100 describes the addition of chemical reducing agents to the reaction product after the phosgenation, but before separating off the solvent. However, such processes usually give only incomplete lightening of the MDI.

A further possible way of lightening the color of MDI comprises addition of additives to the phosgenated crude product. Thus, U.S. Pat. No. 4,465,639 describes the addition of water, EP-A-538 500 describes the addition of carboxylic acids, EP-A-445 602 describes the addition of alkanols and EP-A-467 125 describes the addition of polyethers to the reaction product after the phosgenation. These methods have the disadvantage that the reaction can be accompanied by undesired secondary reactions.

Also known is the treatment of the final MDI product after work-up.

Thus, EP-A-133 538 describes the purification of isocyanates by extraction. EP-A-561 225 and EP-A-676 391 describe the hydrogenative after-treatment of MDI for the purposes of lightening the color, with EP-A-676 391 describing the use of specific hydrogenation catalysts. These processes too, result in incomplete lightening of the isocyanates.

A further possible method of lightening MDI is treatment of the MDA used as raw material. EP-A-546 398 proposes acidifying the MDA with hydrochloric acid prior to the phosgenation. However, the effect of this measure is only slight. EP-A-446 781 describes a process for preparing light-colored MDI by hydrogenative treatment of the MDA. However, the drastic conditions of such a hydrogenation can lead to interfering secondary reactions.

Furthermore, it is possible to alter the process conditions in the preparation of MDA. However, secondary reactions which can lead to a change in the other properties of the MDA cannot be ruled out in such a case.

It is an object of the present invention to develop a process for preparing isocyanates, in particular raw MDI, having a light color, which process is simple, requires no intrusions into the running process and gives an effective lightening of the color.

We have found that this object is achieved by treating the amines with solid inorganic substances which contain Lewis acid and/or Brönsted acid centers and subsequently phosgenating the amines which have been treated in this way.

The present invention accordingly provides a process for preparing isocyanates having a light color by reacting amines with phosgene, wherein the amines are treated with solid inorganic substances containing Lewis acid and/or Brönsted acid centers prior to the reaction with the phosgene.

As solid inorganic substances containing Lewis and/or Brönsted acid centers, particular preference is given to using compounds which have a large internal surface area and can therefore be brought into good contact with the liquid or dissolved amines. Preference is given to using natural, artificially modified and synthetic oxide and/or silicates, in particular aluminosilicates.

Examples of such substances are activated aluminum oxides, activated silicas and silica gels. Preference is given to activated silicates, in particular aluminum silicates such as zeolites, bentonite, kaolinites and montmorillonites. Very particular preference is given to activated materials of the montmorillonite type.

The activation can be carried out thermally or chemically. Chemical activation is described, for example, in P. Kumar et. al., "Evolution of Porosity and Surface Acidity in Montmorillonite Clay on Acid Activation", Ind. Eng. Chem. Res., 1995, 1440–1448.

The substances used according to the present invention can be used not only in their natural form but, particularly preferably, also in artificially modified form, e.g. after chemical treatment with acids or metal ions, as described, for example, in P. Laszlo, "Chemical Reactions on Clays, Science 235, [1987], 1473). The particle size and morphology of the solid inorganic substance is not especially critical for the process of the present invention. However, it is advantageous to use these substances in a macroscopic form which can easily be separated from the amine after the treatment. As a general rule, the finer the inorganic material, the better the color-lightening action and the more difficult the separation, and vice versa. The separation is usually carried out by the customary and known methods for removing solids from liquid systems, for example by means of filtration, centrifugation or decantation.

The solid inorganic substances can be used individually or as mixtures. When using mixtures, it is advantageous for at least one component to come from the group consisting of montmorillonites.

In principle, it would also be possible to use highly polymeric organic substances having Lewis and/or Brönsted acid centers in place of the solid inorganic substances. However, organic compounds play no role here because in the case of the known compounds of this type it is not possible to rule out interfering interactions of the polymer framework with the amines and/or the solvents.

As amines which are subjected to the treatment according to the present invention with the solid inorganic substances, all organic amines which can be reacted with phosgene to give isocyanates are suitable in principle. This treatment is particularly advantageous in the case of aromatic amines, in particular diphenylmethanediamine (MDA) and its higher homologues, since polyphenylenepolymethylene polyisocyanate (raw MDI) is particularly prone to strong discoloration.

The treatment of the amines should be carried out in the liquid phase, in order to ensure sufficient contact between amine and the solid, inorganic substances. Depending on the constitution of the amines it can be advantageous to employ solutions of the amines. Solvents which can be used here are all solvents which are inert toward amines, for example esters such as ethyl acetate or butyl acetate, ethers such as t-butyl methyl ether or ketones such as propanone, butanone or cyclohexanone. However, preference is given to using inert aromatic or aliphatic hydrocarbons or halogenated hydrocarbons, e.g. chlorobenzene, o-dichlorobenzene, toluene, xylenes, alkylbenzenes and alkylnaphthalenes, which are directly suitable for use in the subsequent phosgenation process and in which both the amine and the isocyanate prepared therefrom are soluble, and which are not attacked in the process stages of amine treatment and phosgenation.

The purification process of the present invention can be carried out by suspending the solid inorganic substances in the amine or the amine solution and subsequently separating off the solids. However, it is also possible to arrange the solid as a fixed bed and to pass the amine or the amine solution over it.

The first-named process variant is usually carried out batchwise. Reaction vessels employed here are mixing vessels, for example stirred reactors. After the inorganic solid has acted on the amine, it is separated off as described above.

The treatment by means of a fixed bed is mostly carried out continuously, for example in columns or flow tubes.

The treatment of the amine according to the present invention using inorganic solid substances is preferably carried out at from −10° C. to 100° C., preferably from 10° to 50° C., and a pressure of from 0.1 to 200 bar, preferably from 0.1 to 10 bar. The amount of inorganic solid substance should be from 0.1 to 30% by weight, preferably from 0.5 to 15% by weight, based on the amount of amine. The treatment time is from 1 s to 5 h, preferably from 1 min to 1 h.

The time is dependent, inter alia, on the type of amine used and the effectiveness of the inorganic solid substance and can be determined by comparative experiments.

The solvent can be separated off after the treatment according to the present invention, but this is not absolutely necessary. Since the amine is usually used for preparing isocyanates, it is advantageous for the amine solution, after separating off the solid, inorganic substance to be fed directly to the phosgenation.

The amines treated by the process of the present invention can be reacted without problems to give isocyanates having a color which is significantly lighter than that of isocyanates prepared from untreated amines.

The process of the present invention can be particularly advantageously employed in the preparation of mixtures of diphenylmethane diisocyanate and its higher homologues, known as "raw MDI". The mixture of two-ring and multi-ring MDA used as amine, which is prepared according to known methods by condensation of aniline with formaldehyde in the presence of hydrochloric acid, comprises a large number of compounds which cause the dark color after reaction of the MDA to form MDI. Use of the process of the present invention enabled the color of the raw MDI to be significantly improved. The raw MDI obtained can be processed to give polyurethanes having a light color.

The process of the present invention is simple to carry out and can easily be integrated into existing plants for isocyanate production. Owing to the very gentle treatment, it leads to no secondary reactions in the amine and thus to no impairment of the quality of the isocyanate. After the treatment, the solid inorganic substances can be separated virtually quantitatively from the amine.

After being separated off, the solid inorganic substances can be regenerated by known methods and reused, or they can be discarded.

The invention is illustrated by the following examples:

EXAMPLES 1 to 6

In each case, 150 g of neutralized and dried MDA from the acid condensation of aniline and formaldehyde were dissolved in 30 ml of toluene. 20 g of the inorganic substance corresponding to Table 1 were then added and the solution was stirred for from 10 to 30 minutes. Subsequently, the inorganic substance was separated off by means of a pressure filtration unit at a gauge pressure of nitrogen of 3 bar and the clear filtrate was freed off the solvent toluene under reduced pressure. 100 g of the MDA treated in this way were in each case dissolved in 1 liter of monochlorobenzene and reacted at 50°–80° C. under atmospheric pressure in a 6 liter stirred reactor with 200 g of phosgene, dissolved in 1.3 l of monochlorobenzene, to give the carbamoyl chloride. The temperature of the reaction mixture was increased to 120° C. over a period of 2 hours, during which time the reaction to give the isocyanate occured. The remaining phosgene and the major part of the monochlorobenzene were subsequently taken off and the remaining monochlorobenzene was then removed at 10 mbar and 120° C. The reaction mixture was then drained and subjected to thermal after-treatment at 10 mbar and 180° C. for 45 minutes on a rotary evaporator.

The NCO contents of the MDI samples obtained in this way were determined in accordance with DIN 53 185, the EHC (easily hydrolyzable chlorine) values were determined in accordance with ASTM D 4667-87 and the DHC (difficultly hydrolyzable chlorine) values were determined in accordance with ASTM D 4663-87.

In addition, the iodine color number was determined in accordance with DIN 6162. For this purpose, the samples diluted at 1:5 with monochlorobenzene were examined using a comparator apparatus from Hellige by comparison with color disks corresponding to iodine color numbers. A photometric color number determination was also carried out by means of a photometer from Doktor Lange in the iodine color number mode. The results are recorded in Table 1.

TABLE 1

| Ex. | Additive | NCO (%) | EHC (ppm) | DHC (ppm) | ICN 1:5 *) | CN 1:5 **) |
|---|---|---|---|---|---|---|
| 1 | Montmorillonite K 10 (20 g) | 32.1 | 237 | 758 | 35 | 19 |
| 2 (C) | — | 32.2 | 316 | 915 | 80 | 41 |
| 3 | Silica gel 60 (20 g) | 32.0 | 215 | 820 | 50 | 26 |
| 4 | Montmorillonite K 10 (20 g) | 31.9 | 209 | 736 | 30 | 17 |
| 5 | Molecular sieve 10 A (20 g) | 31.8 | 190 | 730 | 35 | 21 |
| 6 | Montmorillonite KSF (20 g) | 31.6 | 182 | 769 | 50 | 25 |

C Comparative example
ICN Iodine color number
CN Color number determined photometrically
*) measured by means of the comparator
**) measures by means of the photometer

We claim:

1. A process for preparing isocyanates having a light color comprising reacting amines with phosgene, wherein the amines are treated with solid inorganic substances containing Lewis acid and/or Brönsted acid centers prior to the reaction with the phosgene.

2. A process as claimed in claim 1, wherein the solid inorganic substances comprise natural, artificially modified or synthetic oxides and/or silicates.

3. A process as claimed in claim 1, wherein the solid inorganic substances comprise aluminosilicates.

4. A process as claimed in claim 1, wherein the solid inorganic substances comprise montmorillonites.

5. A process as claimed in claim 1, wherein the solid inorganic substances are chemically and/or thermally activated.

6. A process as claimed in claim 1, wherein the process comprises activating the solid organic substances by treating the solid inorganic substances with acids and/or metal ions.

7. A process as claimed in claim 1, wherein the amines are selected from the group consisting of diphenylmethyl-diamine and its higher homologues.

8. A process as claimed in claim 1, wherein the amine treatment step is carried out at from −10° to 100° C. and pressures of from 0.1 to 200 bar.

9. A process as claimed in claim 1, wherein the amine treatment step is carried out at from 10° to 50° C. and pressures of from 0.1 to 10 bar.

10. A process as claimed in claim 1, wherein the amines are dissolved in organic solvents during the amine treatment step.

11. A process for preparing isocyanates having a light color as claimed in claim 1, further comprising separating the solid inorganic substance after the amine treatment step and reacting the amines with phosgene to give the corresponding isocyanate.

12. A process for preparing isocyanate having a light color comprising the steps of:

providing an amine;

treating the amine with a solid inorganic substance containing Lewis acid and/or Brönsted acid center; and reacting the amine with phosgene.

13. A process as claimed in claim 12, wherein the solid inorganic substance comprises a natural, artificially-modified or synthetic oxides or silicate.

14. A process as claimed in claim 12, wherein the solid inorganic substance comprises an aluminosilicate.

15. A process as claimed in claim 12, wherein the solid inorganic substance comprises a montmorillonite.

16. A process as claimed in claim 12, wherein the solid inorganic substance is chemically or thermally activated.

17. A process as claimed in claim 12, wherein the process comprises activating the solid organic substance by treating the solid inorganic substance with an acid and/or metal ion.

18. A process as claimed in claim 12, wherein the amine is selected from the group consisting of diphenylmethyl-diamine and its higher homologues.

19. A process as claimed in claim 12, wherein the amine treatment step is carried out at a temperature of from −10° to 100° C. and a pressure of from 0.1 to 200 bar.

20. A process as claimed in claim 12, wherein the amine treatment step is carried out at a temperature of from 10° to 50° C. and a pressure of from 0.1 to 10 bar.

21. A process as claimed in claim 12, wherein the amine is dissolved in an organic solvent during the amine treatment step.

22. A process for preparing isocyanates having a light color as claimed in claim 12, further comprising separating the solid inorganic substance after the amine treatment step and reacting the amine with phosgene to give the corresponding isocyanate.

\* \* \* \* \*